United States Patent
Hilger et al.

(12) 
(10) Patent No.: US 6,488,909 B1
(45) Date of Patent: Dec. 3, 2002

(54) CHELATING AGENTS AS WELL AS THEIR TRICARBONYL COMPLEXES WITH TECHNETIUM AND RHENIUM

(75) Inventors: Stephan Hilger; Ludger Dinkelborg; Dieter Heldmann; Friedhelm Blume; Dietmar Berndorff, all of Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/468,331

(22) Filed: Dec. 21, 1999

(30) Foreign Application Priority Data

Dec. 21, 1998  (DE) .......................... 198 60 289

(51) Int. Cl.$^7$ .................. A61K 51/00; A61M 36/14
(52) U.S. Cl. ..................... 424/9.1; 534/10; 534/14; 424/1.11; 424/1.65; 424/1.69
(58) Field of Search ................. 534/7, 10–16; 562/400; 424/1.11, 1.65, 1.69, 9.1, 9.3, 9.4, 9.5, 9.6, 9.7, 9.8

(56) References Cited

FOREIGN PATENT DOCUMENTS

| WO | WO 95/05814 | 3/1995 |
| WO | WO-98-48 | * 11/1998 |
| WO | WO 98/48848 | 11/1998 |

OTHER PUBLICATIONS

Yamamura, Norio et al: "Technetium–99m–Labeled Medium–Chain Fatty Acid Analogs Metabolized by.beta.–Oxidation: Radiopharmaceutical for Assessing Liver Function" Bioconjugate Chem., Bd. 10, Nr. 3, 1999, Seiten 489–495, XP002137894.

Database Chemabs/Online/Chemical Abstracts Service, Columbus, Ohio, US Abe Yoshiro et al: "Synthesis and antimicrobial properties of N–substituted amino acid–type amphoterics containing a thio ether linkage" retrieved from STN Database accession No. 85:110387 XP002131480 & Yukagaku (1976), 25(7), 419–23.

Database Chemabs/Online/Chemical Abstracts Service, Columbus, Ohio, US Okada, Hisashi et al: "Composition for processing silver halide color photographic material and photographic processing method" retrieved from STN Database accession No. 118:112883 XP002131481 & JP 04 204533 A (Fuji Photo Film Co., Ltd., Japan) Jul. 24, 1992 (Jul. 24, 1992).

Database Chemabs/Online/Chemical Abstracts Service, Columbus, Ohio, US Okey, R. W. et al: "Predicting stability constants of various chelating agents using QSAR technology" retrieved from STN Database accession No. 129:85331 XP002131482 & Emerging Technol. Hazard. Waste Manage. 7, [Proc. I&EC Div. ACS Symp.] (1997), Meeting Date 1996, 49–68. Editor(s): Tedder, D. William;Pohland, Frederick G. Publisher: Plenum, New York, N.Y.

Database Chemabs/Online/Chemical Abstracts Service, Columbus, Ohio, US Kishimoto, Shinzo et al: "Silver halide color photographic materials" retrieved from STN Database accession No. 107:165332 XP002131483 & JP 61 252552 A (Fuji Photo Film Co., Ltd., Japan) Nov. 10, 1986 (Nov. 10, 1986).

* cited by examiner

*Primary Examiner*—Dameron L. Jones
(74) *Attorney, Agent, or Firm*—Millen, White, Zelano & Branigan, P.C.

(57) ABSTRACT

New chelating agents as well as their tricarbonyl complexes with technetium and rhenium and the use of these compounds in radiodiagnosis and radiotherapy are described. The new chelating agents are coupled to substances that accumulate in the diseased tissue.

31 Claims, No Drawings

CHELATING AGENTS AS WELL AS THEIR TRICARBONYL COMPLEXES WITH TECHNETIUM AND RHENIUM

The invention relates to the field of radiopharmaceuticals and describes new chelating agents as well as their tricarbonyl complexes with technetium and rhenium.

Complexes with radioactive metals have already been used for a very long time in radiodiagnosis and radiotherapy. The radionuclide technetium-99m is used most frequently, since it is especially well suited for in-vivo use because of its advantageous physical properties (no corpuscular radiation, short half-life of 6.02 h, good detectability by its 140 KeV γ-radiation), its short biological half-life and its broad availability. For synthesis of technetium-99m-complexes, pertechnetate is first obtained from a nuclide generator and converted by using suitable reducing agents (e.g., $SnCl_2$) into a lower oxidation stage, which then is stabilized by a suitable chelating agent. Since technetium can be present in a number of oxidation stages (+7 to −1), which can greatly alter the pharmacological properties by altering the charge of a complex, it is necessary to provide chelating agents or complex ligands for technetium-99m, which can bind technetium in a more secure, tight and stable manner in a defined oxidation stage. The chelating agents inhibit redox processes or technetium-release reactions that occur in vivo. Such undesirable reactions make a reliable diagnosis of diseases more difficult, since the build-up of the radiopharmaceutical agent is determined in lesions, while the pharmacokinetics of the radiopharmaceutical agent and its excretion are determined by its metabolites.

For example, cyclic amines are regarded as suitable complexing agents for technetium and rhenium isotopes [Troutner, D. E. et al., J. Nucl. Med. 21, 443 (1980)], but said amines have the drawback that they are able to bind technetium-99m in good yields only starting from a pH>9. $N_2O_2$ systems [Pillai, M. R. A., Troutner, D. E. et al., Inorg. Chem. 29, 1850 (1990)] are undergoing clinical use. Non-cyclic $N_4$-systems, such as, e.g., the HMPAO, have only a low complex stability. Tc-99m-HMPAO, because of its instability [Ballinger, J. R. et al., Appl. Radiat. Isot. 42, 315 (1991); Billinghurst, M. W. et al., Appl. Radiat. Isot. 42, 607 (1991)], must be administered immediately after its labeling, so that the proportion of decomposition products that have a pharmacokinetics and excretion other than the diagnostic agent can be kept small. The radiochemical contaminants impede the detection of the diseases that are to be diagnosed. $N_2S_2$ chelating agents [Bormans, G. et al., Nucl. Med. Biol. 17, 499 (1990)], such as, e.g., ethylene dicysteine [Verbruggen, A. M. et al., J. Nucl. Med. 33, 551 (1992)] comply, with the requirement for adequate stability of the corresponding technetium-99m complex, but radiodiagnostic agents with a purity above 69% form only starting from a pH>9. $N_3S$ systems (Fritzberg, A., EPA 0 173 424 and EPA 0 250 013) form stable technetium-99m complexes, but must be heated to temperatures of about 100° C. to incorporate the radioisotope. Another drawback of the $N_2S_2$ and $N_3S$ systems consists in that the latter are partially excreted quickly and without specific build-up of the organism, so that the latter are used clinically only as renal functional diagnostic agents. They therefore have only a limited suitability. The coupling of such chelates or chelating agents to substances that accumulate selectively in foci of disease cannot be triggered with simple agents, so that the latter are generally distributed non-specifically in the organism.

In recent years, the demand for radiodiagnostic agents and radiotherapeutic agents that accumulate specifically in diseased tissues has increased. This can be achieved if complexing agents can be coupled easily to substances that accumulate selectively in lesions and in this process do not lose their advantageous complexing properties. Since a weakening of the complex stability is observed frequently after a complexing agent is coupled to such a molecule, the previous attempts to couple chelating agents to selectively accumulating substances do not appear to be very satisfactory. The reason lies in the fact that a diagnostically intolerable proportion of the isotope is released from the conjugate in vivo [Brechbiel, M. W. et al., Inorg. Chem. 25, 2772 (1986)]. It is therefore necessary to provide bifunctional complexing agents that carry both functional groups for stable binding of the desired metal ion and one or more other functional groups for binding the selectively accumulating molecule. Such bifunctional ligands make possible a specific, chemically defined binding of technetium or rhenium isotopes to the most varied biological materials even if a so-called prelabeling is performed. Some chelating agents were described that were coupled to, e.g., monoclonal antibodies (e.g., EP 247 866 and EP 188 256) or fatty acids (EP 200 492). As chelating agents, however, the already mentioned $N_2S_2$ systems were used, which were not very suitable because of their poor stability. Since both the properties of the selectively accumulating substances and the mechanisms according to which they are concentrated in lesions are very different, it is also necessary to vary the chelating agents that can be coupled and to be able to adapt the physiological requirements of the coupling partner with respect to its lipophilia and hydrophilia, membrane permeability or impermeability.

To deal with the above-mentioned drawbacks and limitations of the established chelating groups as well as their conjugates with biomolecules, which accumulate selectively in diseased tissues, it has been attempted in recent years to use tricarbonyl-technetium-I compounds and tricarbonyl-rhenium-I compounds for labeling such biomolecules (Lit. R. Alberto et al., Achievements and Prospects of New Radiotracers, 1997, C3, p. 57 (Abstracts)). Since, however, tricarbonyl-technetium-I-triaqua ions and tricarbonyl-rhenium-I-triaqua ions with high stability are bonded non-specifically and quickly by serum proteins, however, it has not yet been possible to synthesize adequately stable conjugates between substances that accumulate selectively in diseased tissues with tricarbonyl-technetium-I complexes and tricarbonyl-rhenium-I complexes.

International Patent Application WO 98/48848 describes a general method for the production of tricarbonyl-technetium-I complexes and tricarbonyl-rhenium-I complexes. Special chelating agents, which can be coupled to biomolecules and with whose aid especially stable complexes are obtained, are not mentioned in this application.

The object of this invention was therefore to develop stable tricarbonyl-technetium-I complexes and tricarbonyl-rhenium-I complexes that can be coupled to various compounds that selectively accumulate in diseased tissues. Another object of the invention was to provide such chelating agents or complexes that can be coupled and that have a large chemical range of variation of the substituents so as to be able to adapt the latter to the above-referenced requirements. Another aspect of the invention relates to processes for the production of the compounds as well as the pharmaceutical agents that contain the compounds.

This object is achieved by the compounds of general formula (I)

$$Y-CR^1R^2-(CR^3R^4)_n-N(CR^5R^6-COOR^7)-CR^8R^9$$
$$CO-X$$

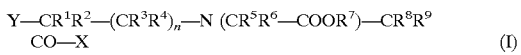

in which
n stands for numbers 0, 1 or 2;

$R^1$, $R^2$, $R^3$, $R^4$, $R^5$, $R^6$, $R^8$ and $R^9$ are the same or different and in each case represent a hydrogen atom or an unbranched, branched, cyclic or polycyclic $C_1$–$C_{60}$ alkyl, $C_1$–$C_{60}$ alkenyl, $C_5$–$C_{60}$ polyalkenyl, $C_1$–$C_{60}$ alkinyl; $C_5$–$C_{60}$ polyalkinyl, $C_5$–$C_{60}$ aryl, $C_5$–$C_{60}$ alkylaryl or $C_5$–$C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

$R^7$ stands for a hydrogen atom or an alkali cation or an alkaline-earth cation or a primary, secondary or tertiary ammonium ion;

x represents a radical O—$R^7$ or means a radical $NR^{10}R^{11}$, in which $R^{10}$ and $R^{11}$ are the same or different and in each case represent a hydrogen atom or an unbranched, branched, cyclic or polycyclic $C_1$–$C_{60}$ alkyl, $C_1$–$C_{60}$ alkenyl, $C_5$–$C_{60}$ polyalkenyl, $C_1$–$C_{60}$ alkinyl, $C_5$–$C_{60}$ polyalkinyl, $C_5$–$C_{60}$ aryl, $C_5$–$C_{60}$ alkylaryl or $C_5$–$C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se; or $R^{10}$ and/or $R^{11}$ are the same or different and in each case represent a hydrogen atom, a peptide radical, protein radical, a modified or unmodified DNA or RNA oligonucleotide radical, a modified or unmodified aptamer radical or a PNA radical;

Y stands for an $R^{12}$—S radical, in-which $R^{12}$ represents a hydrogen atom or an unbranched, branched, cyclic or polycyclic $C_1$–$C_{60}$ alkyl, $C_1$–$C_{60}$ alkenyl, $C_5$–$C_{60}$ polyalkenyl, $C_1$–$C_{60}$ alkinyl, $C_5$–$C_{60}$ polyalkinyl, $C_5$–$C_{60}$ aryl, $C_5$–$C_{60}$ alkylaryl or $C_5$–$C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se; or $R^{12}$ represents a peptide radical, protein radical, a modified or unmodified DNA or RNA-oligonucleotide radical, a modified or unmodified aptamer radical or a PNA radical;

or Y stands for an $R^{13}R^{14}P$ radical, in which $R^{13}$ and $R^{14}$ are the same or different and in each case represent a hydrogen atom or an unbranched, branched, cyclic or polycyclic $C_1$–$C_{60}$ alkyl, $C_1$–$C_{60}$ alkenyl, $C_5$–$C_{60}$ polyalkenyl, $C_1$–$C_{60}$ alkinyl, $C_5$–$C_{60}$ polyalkinyl, $C_5$–$C_{60}$ aryl, $C_5$–$C_{60}$ alkylaryl radical or $C_5$–$C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

or Y stands for a monocyclic or polycyclic heteroaromatic compound, which contains at least one heteroatom from the series O, S, N and/or P; and their complexes with tricarbonyl-technetium-I radicals or tricarbonyl-rhenium-I radicals of the corresponding radioisotopes.

Preferred are those compounds in which radicals $R^1$, $R^2$, $R^3$, $R^4$, $R^5$, $R^6$, $R^8$ and $R^9$ in each case represent a hydrogen atom. Those compounds are also preferred in which $R^7$ stands for a hydrogen atom or an alkali cation or an alkaline-earth cation.

Radical Y preferably stands for a monocyclic heteroaromatic compound or a radical $R^{12}$—S, in which $R^{12}$ preferably stands for an unbranched, branched, cyclic or polycyclic, saturated or unsaturated $C_1$–$C_{60}$ alkyl radical. Especially preferred are those compounds in which radical $R^{12}$ represents a $C_1$–$C_{10}$ alkyl chain.

Radical X preferably stands for a group O—$R^7$, in which $R^7$ stands for a hydrogen atom or an alkali cation or an alkaline-earth cation or a primary, secondary or tertiary ammonium ion. Radical X also preferably stands for a group $NR^{10}R^{11}$, in which $R^{10}$ and $R^{11}$ are the same or different and in each case represent a hydrogen atom, a peptide radical, protein radical, a modified or unmodified DNA or RNA-oligonucleotide radical, a modified or unmodified aptamer radical or a PNA radical, or for a group $NR^{10}R^{11}$ in which $R^{10}$ and $R^{11}$ are the same or different and in each case stand for a hydrogen atom, an unbranched, branched, cyclic or polycyclic, saturated or unsaturated $C_1$–$C_{60}$ alkyl radical.

The production of the compounds of general formula (I) according to the invention is carried out in that compounds of general formula (II) are reacted with compounds of general formula (III) according to the reaction diagram below:

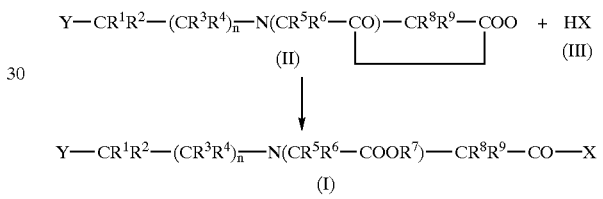

in which $R^1$, $R^2$, $R^3$, $R^4$, $R^5$, $R^6$, $R^7$, $R^8$ and $R^9$ have the above-indicated meaning, and H in HX stands for a proton.

The production of the technetium-99m complexes or Re-tricarbonyl complexes according to the invention is carried out by reaction of the previously synthesized technetiumtricarbonyl precursors or rhenium tricarbonyl precursors [R. Alberto et al., Achievements and Prospects of New Radiotracers, 1997, C3, p. 57 (Abstracts)] with the tridentates according to the invention.

Other objects of the invention are compounds of general formula (IV)

in which n stands for numbers 0, 1 or 2;

$R^1$, $R^2$, $R^3$, $R^4$, $R^5$, $R^6$, $R^8$ and $R^9$ are the same or different and in each case represent a hydrogen atom or an unbranched, branched, cyclic or polycyclic $C_1$–$C_{60}$ alkyl, $C_1$–$C_{60}$ alkenyl, $C_5$–$C_{60}$ polyalkenyl, $C_1$–$C_{60}$ alkinyl, $C_5$–$C_{60}$ polyalkinyl, $C_5$–$C_{60}$ aryl, $C_5$–$C_{60}$ alkylaryl or $C_5$–$C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

X represents a radical O—$R^7$ or means a radical $NR^{10}R^{11}$, in which $R^{10}$ and $R^{11}$ are the same or different and in each case represent a hydrogen atom or an unbranched, branched, cyclic or polycyclic $C_1$–$C_{60}$ alkyl, $C_1$–$C_{60}$ alkenyl, $C_1-C_{60}$ polyalkenyl, $C_1-C_{60}$ alkinyl, $C_5-C_{60}$ polyalkinyl, $C_5-C_{60}$ aryl, $C_5-C_{60}$ alkylaryl or $C_5-C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se; or $R^{10}$ and/or $R^{11}$ are the same or different and in each case represent a hydrogen atom, a peptide radical, protein radical, a modified or unmodified DNA or RNA-oligonucleotide radical, a modified or unmodified aptamer radical or a PNA radical;

Y stands for an $R^{12}$—S radical, in which $R^{12}$ represents a hydrogen atom or an unbranched, branched, cyclic or polycyclic $C_1-C_{60}$ alkyl, $C_1-C_{60}$ alkenyl, $C_5-C_{60}$ polyalkenyl, $C_1-C_{60}$ alkinyl, $C_5-C_{60}$ polyalkinyl, $C_5-C_{60}$ aryl, $C_5-C_{60}$ alkylaryl or $C_5-C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se; or $R^{12}$ represents a peptide radical, protein radical, a modified or unmodified DNA or RNA oligonucleotide radical, a modified or unmodified aptamer radical or a PNA radical;

or Y stands for an $R^{13}R^{14}P$ radical, in which $R^{13}$ and $R^{14}$ are the same or different and in each case represent a hydrogen atom or an unbranched, branched, cyclic or polycyclic $C_1-C_{60}$ alkyl, $C_1-C_{60}$ alkenyl, $C_5-C_{60}$ polyalkenyl, $C_1-C_{60}$ alkinyl, $C_5-C_{60}$ polyalkinyl, $C_5-C_{60}$ aryl, $C_5-C_{60}$ alkylaryl or $C_5-C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

or Y stands for a monocyclic or polycyclic heteroaromatic compound that contains at least one heteroatom from the series O, S, N and/or P;

Z stands for an $R^{12}$—S radical, in which $R^{12}$ represents a hydrogen atom or an unbranched, branched, cyclic or polycyclic $C_1-C_{60}$ alkyl, $C_1-C_{60}$ alkenyl, $C_5-C_{60}$ polyalkenyl, $C_1-C_{60}$ alkinyl, $C_5-C_{60}$ polyalkinyl, $C_5-C_{60}$ aryl, $C_5-C_{60}$ alkylaryl or $C_5-C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

or Z stands for an $R^{13}R^{14}P$ radical, in which $R^{13}$ and $R^{14}$ are the same or different and in each case represent a hydrogen atom or an unbranched, branched, cyclic or polycyclic $C_1-C_{60}$ alkyl, $C_1-C_{60}$ alkenyl, $C_5-C_{60}$ polyalkenyl, $C_1-C_{60}$ alkinyl, $C_5-C_{60}$ polyalkinyl, $C_5-C_{60}$ aryl, $C_5-C_{60}$ alkylaryl or $C_5-C_{60}$ arylalkyl radical, which optionally is substituted with hydroxy, oxo, carboxy, aminocarbonyl, alkoxycarbonyl, amino, aldehyde or alkoxy groups with up to 20 carbon atoms and/or optionally is interrupted and/or substituted by one or more heteroatoms from the series O, N, S, P, As, Se;

or Z stands for a monocyclic or polycyclic heteroaromatic compound, which contains at least one heteroatom from the series O, S, N and/or P;

as well as their complexes with tricarbonyl-technetium-I radicals or tricarbonyl-rhenium-I radicals of the corresponding radioisotopes.

Preferred are those compounds in which radicals $R^1$, $R^2$, $R^3$, $R^4$, $R^5$, $R^6$, $R^8$ and $R^9$ in each case represent a hydrogen atom. Radical Y preferably stands for a radical $R^{12}$—S, in which $R^{12}$ preferably stands for an unbranched, branched, cyclic or polycyclic, saturated or unsaturated $C_1-C_{60}$ alkyl radical. Especially preferred are those compounds in which radical $R^{12}$ represents a $C_1-C_{10}$ alkyl chain.

Radical X preferably stands for a group O—$R^7$, in which $R^7$ stands for a hydrogen atom or an alkali cation or an alkaline-earth cation or a primary, secondary, or tertiary ammonium ion. In addition, radical X preferably stands for a group $NR^{10}R^{11}$, in which $R^{10}$ and $R^{11}$ are the same or different and in each case represent a hydrogen atom, a peptide radical, protein radical, a modified or unmodified DNA or RNA-oligonucleotide radical, a modified or unmodified aptamer radical or a PNA radical, or for a group $NR^{10}R^{11}$, in which $R^{10}$ and $R^{11}$ are the same or different and in each case stand for a hydrogen atom, an unbranched, branched, cyclic or polycyclic, saturated or unsaturated $C_1-C_{60}$ alkyl radical.

Radical Z preferably stands for an $R^{12}$—S radical, in which $R^{12}$ preferably represents a $C_1-C_{10}$ alkyl chain.

The production of the compounds of general formula (IV) according to the invention is carried out in that compounds of general formula (V) are reacted with compounds of general formula (III) according to the reaction diagram below:

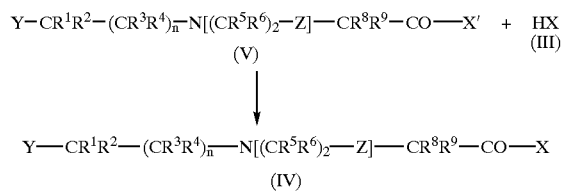

in which $R^1$, $R^2$, $R^3$, $R^4$, $R^5$, $R^6$, $R^7$, $R^8$ and $R^9$ have the meaning that is indicated above, X' stands for a leaving group, such as, e.g., a halogen atom, and H in HX stands for a proton.

The production of the technetium-99m- or Re-tricarbonyl complexes according to the invention is carried out by reaction of the previously synthesized technetiumtricarbonyl precursors or rheniumtricarbonyl precursors [R. Alberto et al., Achievements and Prospects of New Radiotracers, 1997, C3, p. 57 (Abstracts)] with the tridentates according to the invention.

Other objects of the invention are radiopharmaceutical compositions for non-invasive in-vivo visualization of receptors and receptor-containing tissues, which contain a compound of general formula (I) or a compound of general formula (IV) as well as additives that are optionally commonly used in galenicals. The radiopharmaceutical composition is administered to a patient in an amount of 0.1 mCi to 1 Ci, preferably 1 mCi to 500 mCi per 70 kg of body weight. The radiation that is given off by the patient is recorded with a gamma-camera.

Surprisingly enough, the chelates that are synthesized and labeled with Tc-99m tricarbonyl or Re-tricarbonyl showed a higher stability than comparable $N_3S$ and $N_2S_2$ systems, which were described in the literature. Thus, e.g., in a substance according to the invention (Example 2b), no decomposition products were observed after 26 hours of incubation in serum. The complexes are stable, so that at room temperature, no exchange of chelating agents for histidine is carried out. The. chelates and tricarbonyl-Tc-99m and Re-tricarbonyl complexes that are described in this invention are thus clearly better suited for diagnostic and therapeutic purposes than the previously known systems. A special advantage of the compounds according to the invention consists in the fact that their syntheses can be directed without using sulfur protective groups. This makes their synthesis very simple, and in addition, such compounds that are described according to the invention in particular offer the advantage that after radiochemical labeling, no further foreign molecules are contained in the solutions that are to be administered intravenously for radiodiagnosis or radiotherapy. Such foreign molecules frequently disrupt the biodistribution of the radiopharmaceutical agent and can adversely affect the diagnostic information content of the SPECT imaging. In addition, the labelings on such ligands or their coupling products can be performed on substances that accumulate selectively on diseased tissues under very mild conditions. The labeling of the ligands according to the invention or the coupling products on substances that accumulate selectively in diseased tissues is possible at room temperature and at physiologic pH, without the protective groups first being cleaved under the action of bases, acids or other adjuvants that are known to one skilled in the art. This ensures that the frequently very sensitive substances that accumulate selectively in diseased tissues are not chemically altered by such adjuvants, which frequently reduces their selective accumulation in the diseased tissue and thus would adversely affect the information content of the SPECT images.

The coupling to substances that accumulate selectively in diseased tissues is carried out according to the methods that are known to one skilled in the art [e.g., Fritzberg et al.; J. Nucl. Med. 26, 7 (1987)], for example by reaction of electrophilic groups of the complex ligand according to the invention with nucleophilic centers of the substances that accumulate selectively in diseased tissues. Otherwise, nucleophilic groups of the chelating agent are coupled with electrophilic groups of the substances that accumulate selectively in diseased tissues.

As coupling partners, i.a., various biomolecules are provided as well as biological ligands, which bind to specific receptors and thus can be detected in tissue whose receptor density is altered. These include, e.g., modified or unmodified peptides, unmodified or modified proteins, steroid hormones or derivatives thereof, growth factors, neutrotransmitters, modified DNA or RNA oligonucleotides and modified or unmodified aptamers or PNA molecules.

The production of the pharmaceutical agents according to the invention is carried out in a way that is known in the art, by the complexing agents according to the invention being dissolved in aqueous medium optionally with the addition of the additives that are commonly used in galenicals and then sterilized by filtration. Suitable additives are, for example, physiologically harmless buffers, additions of electrolytes (e.g., sodium chloride) and optionally stabilizers. The pharmaceutical agent according to the invention is present in the form of a solution or in freeze-dried form and is mixed shortly before administration with a solution of a Tc-99m tricarbonyl precursor or Re-tricarbonyl precursor.

In the nuclear-medicine in-vivo use, the agents according to the invention are injected intravenously, intraarterially, peritoneally or intratumorally.

The examples below are used for a more detailed explanation of the subject of the invention.

EXAMPLE 1

Production of a Chelating Agent of General Formula (I)

Example 1a

N,N-Bis-(tert-butoxycarboxy-methyl)-S-ethyl-2-mercaptoethylamine 3.52 g (10 mmol) of N,N-bis-(tert-butoxycarboxy-methyl)-2-bromoethylamine is dissolved in 50 ml of absolute dichloromethane and mixed with 1.29 g (10 mmol) of diisopropylethylamine and 0.621 g (10 mmol) of ethylmercaptan. The reaction mixture is refluxed overnight. Then, the solution is extracted twice with semi-saturated, aqueous sodium bicarbonate solution. The organic phase is dried on sodium sulfate, and the solvent is evaporated in a vacuum. The residue is chromatographed on silica gel (eluant: dichloromethane/methanol 99:1).

Yield: 1.82 g (54.6%), white foam

Elementary analysis:

| C 57.63 | H 9.37 | N 4.20 | O 19.19 | S 9.61 |
|---|---|---|---|---|
| C 57.43 | H 9.57 | N 4.12 | O | S 9.32 |

Example 1b

N,N-Bis-(hydroxycarboxy-methyl)-S-ethyl-2-mercaptoethylamine-hydrochloride 1.67 g (5 mmol) of N,N-bis-(tert-butoxycarboxy-methyl)-S-ethyl-2-mercaptoethylamine is dissolved in 12 ml of tetrahydrofuran and mixed with 6 ml of concentrated hydrochloric acid. The resulting reaction mixture is stirred for 1 hour at room temperature and concentrated by evaporation in a vacuum. The residue is pulverized with 10 ml of absolute diethyl ether. Then, the product is filtered off and dried in a medium-high vacuum.

Yield: 1.52 g (59%), white powder.

Elementary analysis:

| C 37.28 | H 6.26 | N 5.44 | O 24.83 | S 12.44 | Cl 13.76 |
|---|---|---|---|---|---|
| C 37.02 | H 6.43 | N 5.16 | O | S 12.20 | Cl 13.52 |

Example 1c

N-(S-Ethyl-2-mercapto-eth-1-yl)-1-aza-4-oxa-3,5-dioxo-cyclohexane-hydrochloride 773.2 mg (3 mmol) of N,N-bis-(hydroxycarboxy-methyl)-S-ethyl-2-mercaptoethylamine-hydrochloride is dissolved in 25 ml of absolute dimethylformamide. 619 mg (2 mmol) of dicyclohexylcarbodiimide, dissolved in 5 ml of absolute dimethylformamide, is added in drops to the reaction batch. The resulting solution is stirred for 1 hour at room temperature. After the precipitated dicyclohexylurea is filtered off, the solution of the cyclic anhydride can be used for coupling to amino-group-carrying molecules/biomolecules. The solution is 0.1 mol of cyclic anhydride.

EXAMPLE 2

Production of a Tricarbonyl-Technetium Complex and a Tricarbonyl-Rhenium Complex with a Chelating Agent of General Formula (I) That is Couple to Propylamine Example 2a N-(Hydroxycarboxy-methyl)-N-(N'-propyl-carbamido-methyl) -8-ethyl-2-mercaptoethylamine 30 ml of the solution of N-(S-ethyl-2-mercapto-eth-1-yl)-1-aza-4-oxa-3,5-dioxo-cyclohexane-hydrochloride that is described under Example 1c is mixed with 303.6 mg (3 mmol) of triethylamine and 177.3 g (3 mmol) of propylamine. It is stirred for 1 hour at room temperature, the solvent is evaporated in a vacuum, and the residue is chromatographed on silica gel (eluant: dichloromethane/methanol 92:8).

Yield: 617 mg (78.4%), white powder.

Elementary analysis:

| C 50.36 | H 8.45 | N 10.68 | O 18.29 | S 12.22 |
|---------|--------|---------|---------|---------|
| C 50.18 | H 8.66 | N 10.41 | O       | S 12.03 |

Example 2b

Tc-99m-Tricarbonyl complex of N-(hydroxycarboxy-methyl)-N-(N'-propyl-carbamido-methyl)-S-ethyl-2-mercaptoethylamine 1 mg of N-(hydroxycarboxy-methyl)-N-(N'-propyl-carbamido-methyl)-S-ethyl-2-mercaptoethylamine is dissolved in 1 ml of 0.1 M disodium phosphate buffer (pH =8.5). Then, 370 MBq of [$^{99m}$Tc(OH$_2$)$_3$(CO)$_3$]$^+$ solution [produced in a way similar to R. Alberto et al., Achievements and Prospects of New Radiotracers, 1997, C3, p. 57 (Abstracts)] is added and incubated for 30 minutes at room temperature. The radiochemical yield and the radiochemical purity of the radiopharmaceutical agent is examined with use of HPLC (>91%).

Example 2c

Stability Study of the Tc-99m-tricarbonyl Complex of N-(hydroxycarboxymethyl)-N-(N'-propylcarbamidomethyl)S-ethyl-2-mercaptoethylamine The solution that is produced according to Example 2b is mixed with 10 mg of histidine and stirred for 1 hour at 50° C. Then, the radiochemical composition is studied with HPLC on an RP18 column: the chromatogram is unchanged. The tricarbonyl complex with histidine that is produced for comparison purposes has considerably shorter retention times.

Example 2d

Production of the Rhenium-tricarbonyl Complex of N-(hydroxycarboxy-methyl)-N-(N'-propylcarbamidomethyl)-S-ethyl-2-mercaptoethylamine 49.3 mg of tetrabutylammonium perrhenate and 139 mg of tetrabutylammonium chloride are dissolved in 5 ml of diethylene glycol-dimethyl ether, the solution is saturated with carbon monoxide, and 1.5 ml of a 1 mol borane solution in THF is added in drops under CO atmosphere. It is stirred for 4 more hours at an oil bath temperature of 110° C., and in this case, a slower flow of CO gas is sent through. After cooling, a solution of 39.3 mg of N-(hydroxycarboxymethyl)-N-(N'-propylcarbamidomethyl)-S-ethyl-2-mercaptoethylamine in 1 ml of THF is added in drops to the solution that is thus produced, and then it is refluxed for 30 minutes. The reaction mixture is concentrated by evaporation, and the residue is purified by chromatography with the solvent 90% methylene chloride and 10% methanol.

Yield: 33.7 mg =63.6%. Structural detection spectroscopically by NMR, IR and MS.

EXAMPLE 3

Production of a Tricarbonyl-Technetium Complex with a Chelating Agent of General Formula (I) that is Coupled to an Oligonucleotide

Example 3a

5'-(6-Aminohexylphosphato)-GGAGfUfCfUfUAGGfCAGfCGfCGfUfUfUfUfCG AGfCfUAfCfUfCfC-3'-3'-dT (f: 2'-F)

The 33-mer oligonucleotide GGAGfUfCfUfUAGGf-CAGfCGfCGfUfUfUfUfCGAGfCfUAfCfUfCfC (f: 2'-F) was produced in 3'-3'-dT capped form in the usual way by means of an automatic synthesis machine from the Pharmacia Company (see Oligonucleotides and Analogues, A Practical Approach, Ed. F. Eckstein, Oxford University Press, Oxford, New York, Tokyo, 1991), whereby the oligonucleotide was still on the column of the solid vehicle. By reaction with trichloroacetic acid in dichloromethane, the 5'-hydroxyl group was released. The load on the column was about 10 mg in 34-mer. To link the amino linker, the column was reacted with a solution of 50 μmol of β-cyanoethyl-N, N-diisopropylamino-6-(trifluoroacetamido)-1-hexyl-phosphoroamidite [produced according to Nucl. Acids. Res. 16, 2659–2669 (1988)] in the presence of tetrazole. The oxidation of the phosphite formed into completely protected phosphotriester was carried out with iodine in tetrahydrofuran/pyridine/water. The cleavage of the oligonucleotide from the vehicle and the cleavage of the protective groups took place according to standard processes (see Oligonucleotides and Analogues, A Practical Approach, Ed. F. Eckstein, Oxford University Press, Oxford, New York, Tokyo, 1991, p. 36). The crude oligonucleotide was liberated of TBAF traces by dialysis and then purified by RP chromatography. The title compound was obtained by freeze-drying.

Yield: 6.5 mg, white powder.

Example 3b

Conjugation of Oligonucleotide 3a with 1c

5'-[Et-S —CH$_2$—CH$_2$—N(CH$_2$—COOH)—CH$_2$—CO—NH—(CH$_2$)$_6$—O-phosphato)-GGAGfUfCfUfUAGGfCAGfCGfCGfUfUfUfUfCGAGf CfUAfCfUfCfC-3'-3'-dT (f: 2'-F)

5 mg of the oligonucleotide that is obtained in Example 1d is dissolved in 1 ml of NaHCO$_3$/Na$_2$CO$_3$ buffer (pH 9, 0.2M) and mixed with 100 μl of the solution of N-(S-ethyl-2-mercapto-eth-1-yl)-1-aza-4-oxa-3,5-dioxo-cyclohexane-hydrochloride in DMF that is produced under Example 1c. It is stirred for 3 hours at room temperature, the pH is set at 7.2 by adding 0.01 M hydrochloric acid, and the conjugate is precipitated by adding 9 ml of ethanol at −70° C. The purification of the title compound took place by RP chromatography.

Yield: 1.1 mg, white powder.

Example 3c

Tc-99m-Tricarbonyl Complex of Oligonucleotide 3b

100 μg of 5'-[Et-S—CH$_2$—CH$_2$—N(CH$_2$—COOH)—CH$_2$—CO—NH—(CH$_2$)$_6$—O—phosphato)-

GGAGfUfCfUfUAGGfCAGfCGfCGfUfUfUfUfCGAGf CfUAfCfUfCfC-3'-3'-dT (f=2'-F) is dissolved in 150 µl of disodium hydrogen phosphate buffer (pH=8.5, 0.1M). It is mixed with 180 MBq of [$^{99m}$Tc (OH$_2$)$_3$(CO)$_3$]$^+$ solution [produced in a way similar to R. Alberto et al., Achievements and Prospects of New Radiotracers, 1997, C3, p. 57 (Abstracts)], and the reaction mixture is allowed to stand for 30 minutes at room temperature. The labeling yield is determined by means of HPLC and PAGE analysis and is >90%.

EXAMPLE 4

Production of a Tricarbonyl-Technetium Complex with a Chelating Agent of General Formula (I) that is Coupled to Bovine Serum Albumin

Example 4a

Conjugation of the protein bovine serum albumin (BSA) with 1c: Et-S—CH$_2$—CH$_2$—N(CH$_2$—COOH)—CH$_2$—CO-BSA 5 mg of BSA is dissolved in 500 µl of 0.1M disodium phosphate buffer (pH=8.5). 100 µl of the solution of N-(S-ethyl-2-mercapto-eth-1-yl)-1-aza-4-oxa-3,5-dioxo-cyclohexane-hydrochloride in DMF is added, and it is stirred for 2.5 hours at room temperature. Unreacted 1c is removed from the conjugate by dialysis on PBS. The solution of 4a that is thus prepared can be further used without further purification.

Yield: 3.5 mg of conjugate per 1.3 ml of PBS

Example 4b

Tc-99m-Tricarbonyl Complex of Protein 4a 1 mg (371 µl) of conjugate 4a is mixed with 180 MBq of [$^{99m}$Tc(OH$_2$)$_3$(CO)$_3$]$^+$ solution (produced in a way similar to R. Alberto et al., Achievements and Prospects of New Radiotracers, 1997, C3, p. 57 (Abstracts)]. The reaction mixture is allowed to stand for 60 minutes at room temperature. The labeling yield is determined by means of SE-HPLC and is >90%.

EXAMPLE 5

Production of a Tricarbonyl-Technetium Complex with a Chelating Agent of General Formula (I) that is Coupled to a Peptide

Example 5a

Conjugation of peptide Phe-(D-Trp)-Leu-Asp-Ile-Ile-Trp-OH with 1c: Et-S—CH—CH—N(CHC—COOH)—CH—CO—Phe-(D-Trp)-Leu-Asp-Ile-Ile-Trp-OH 5 mg of peptide Phe-(D-Trp)-Leu-Asp-Ile-Ile-Trp-OH (produced analogously to E. Atherton & R. C. Sheppard, Solid Phase Peptide Synthesis, IRL PRESS 1989, Oxford) is dissolved in 0.5 ml of absolute dimethylformamide and mixed with 1.52 mg of triethylamine. Then, 100 µl of the solution of N-(S-ethyl-2-mercapto-eth-1-yl)-1-aza-4-oxa-3,5-dioxo-cyclohexane-hydrochloride in DMF is added, and it is stirred for 3.5 hours at room temperature. The conjugate is purified by RP chromatography and isolated by freeze-drying.

Yield: 2.3 mg (38.5%), white powder.
FAB-MS: 1197

Example 5b

Tc-99m-Tricarbonyl Complex of Peptide 5a 1 mg of conjugate 5a is mixed with 180 MBq of [$^{99m}$Tc (OH$_2$)$_3$(CO)$_3$]$^+$ solution [produced in a way similar to R. Alberto et al., Achievements and Prospects of New Radiotracers, 1997, C3, p. 57 (Abstracts)]. The reaction mixture is allowed to stand for 30 minutes at room temperature. The labeling yield is determined by means of SE-HPLC and is >90%.

EXAMPLE 6

Production of a Chelating Agent of General Formula (I)

Example 6a

Production of di-t.-butyl-2,2'-{[2-(1H-pyrazol-1yl)-ethyl]-imino}-diacetate 1 g of N-(2-bromoethyl)-iminodiacetic acid-di-t-butylester, dissolved in 10 ml of methylene chloride, is mixed with 213 mg of pyrazole and mixed with a mixture of 1 ml of 40% aqueous tetrabutylammonium hydroxide solution and 1.14 ml of 5 molar sodium hydroxide solution. The mixture is stirred vigorously for 18 hours at room temperature under a cover gas. For working-up, the phases are separated, the organic phase is washed several times with water, dried with sodium sulfate and concentrated by evaporation. The residue is purified by chromatography in a mobile solvent system of methylene chloride/methanol.

Yield: 318 mg=33% oil

Detection spectroscopically by NMR, IR and MS

Example 6b

Production of [2-(1H-pyrazol-1-yl)-ethylimino]-diacetic acid, trifluoroacetate 330 mg of di-t.-butyl-2,2'-{[2-(1H-pyrazol-1-yl)-ethyl]-imino}-diacetate (Example 6a) is dissolved in 3.3 ml of trifluoroacetic acid and stirred for 2 hours at room temperature. After the solution is concentrated by evaporation under high vacuum, the residue is stirred with ether. After renewed drying under high vacuum, 281 mg of solid (85%) remains.

Detection spectroscopically by NMR, IR and MS

EXAMPLE 7

Production of a Tricarbonyl-Technetium Complex with a Chelating Agent of General Formula (I) that is Coupled to Propylamine

Example 7a

Production of {2-(1H-pyrazol-1-yl)-ethylimino}-diacetic Acid-monopropylamide 268 mg of [2-(1H-pyrazol-1-yl)-ethylimino]-diacetic acid, trifluoroacetate (Example 6b) is dissolved in 20 ml of DMF and mixed with 110 µl of triethylamine. Then, 162 mg of dicyclohexylcarbodiimide, dissolved in 3 ml of DMF, is slowly added in drops under a cover-gas atmosphere and then stirred for 16 hours at room temperature. 65 µl of propylamine, dissolved in 3 ml of DMF, is added in drops to the cloudy solution, the batch is stirred for 1 hour, then 65 µl of propylamine is added in pure form, and the batch is stirred for 2 more hours. The precipitated solid is filtered off, the solution is concentrated by evaporation, and the residue is purified by chromatography in the methylene chloride/methanol system. Yield 48 mg 23%

Detection spectroscopically by NMR, IR and MS

Example 7b

Tc-99m-Tricarbonyl Complex of {2-(1H-pyrazol1-yl)-ethylimino}-diacetic Acid-monopropylamide 2 mg of {2-(1H-pyrazol-1-yl)-ethylimino}-diacetic acid-monopropylamide (Example 7a) is dissolved in 1 ml of 0.1M disodium phosphate buffer (pH=8.5) and mixed with 37 MBq of $[^{99m}Tc(OH)_3(CO)_3]^+$ solution, produced in a way similar to R. Alberto et al., Achievements and Prospects of New Radiotracers, 1997, C3, p. 57 (Abstracts). It is incubated for 30 minutes at room temperature and then analyzed by means of HPLC: radiochemical purity>90%.

Example 7c

Stability Study of the Tc-99m-tricarbonyl Complex of {2-(1H-pyrazol-1-yl)-ethylimino}-diacetic Acid-monopropylamide The solution that is produced according to Example 7b is mixed with 20 mg of histidine and stirred for 1 hour at 50° C. Then, the radiochemical composition is studied with HPLC on an RP18 column: the chromatogram is unchanged. The tricarbonyl complex with histidine that is produced for comparison purposes has considerably shorter retention times.

EXAMPLE 8

Production of a Chelating Agent of General Formula (IV)

Example 8a

Production of S-methyl-thioglycolic Acid-N-(2-methylthioethyl)-amide 6 ml of 2-methylthio-ethylamine is dissolved in 250 ml of methylene chloride, mixed with 6.84 g of S-methyl-thioglycolic acid and with 7.42 g of N-hydroxysuccinimide and mixed drop by drop with 13.3 g of dicyclohexylcarbodiimide in 250 ml of methylene chloride under a cover-gas atmosphere. It is stirred, for 3 more hours at room temperature. The precipitate is filtered off, the filtrate is washed twice with semi-saturated sodium bicarbonate solution and once with water, dried with sodium sulfate and concentrated by evaporation. The residue is purified by chromatography with the mobile solvent system of methylene chloride/methanol: Yield 10 g=86.7% of theory.

Example 8b

Production of bis-(2-methylthioethyl)-amine 5.18 g of S-methyl-thioglycolic acid-N-(2-methylthioethyl)-amide (Example 8a) is dissolved in 350 ml of tetrahydrofuran and added in drops to a suspension of 5.48 g of lithium aluminum hydride in 350 ml of tetrahydrofuran under a cover-gas atmosphere. Then, it is refluxed for 18 hours. While being cooled in an ice bath, the excess lithium aluminum hydride is carefully hydrolyzed by adding 100 ml of water in drops, it is stirred for 1 more hour, and then another 700 ml of water is added. The solution is extracted three times with methylene chloride/methanol 10/1, and the combined organic phases are washed with water one time. After concentration by evaporation, the residue is purified by chromatography with the mobile solvent system of methylene chloride/methanol: yield 1.5 g=32% of theory.

Example 8c

Production of N,N-bis-(2-methylthioethyl)-glycine methyl ester 165 mg of bis-(2-methylthioethyl)-amine (Example 8b) is dissolved in 20 ml of acetonitrile and mixed with 174 μl of diisopropylethylamine. 92.7 μl of bromoacetic acid methyl ester, dissolved in 20 ml of acetonitrile, is added in drops under a cover-gas atmosphere, and the batch is stirred for 18 hours at room temperature. The acetonitrile is drawn off, the residue is taken up with methylene chloride and washed twice with saturated sodium bicarbonate solution. The organic phase is dried with sodium sulfate and concentrated by evaporation, and the residue is purified by chromatography with the mobile solvent system of methylene chloride/methanol: Yield 183 mg=77% of theory.

EXAMPLE 9

Production of a Tricarbonyl-Technetium Complex with a Chelating Agent of General Formula (IV) that is Coupled to Propylamine

Example 9a

Production of N,N-bis-(2-methylthioethyl)-glycine-N'-propylamide 170 mg of N,N-bis-(2-methylthioethyl)-glycine methyl ester is dissolved in 7 ml of propylamine, and 14 mg of 2-hydroxypyridine is added under cover gas. The batch is heated for 19 hours to 70° C. The solution is concentrated by evaporation, the residue is taken up with methylene chloride and washed with sodium bicarbonate solution. The aqueous phases are combined and reextracted with ethyl acetate, the combined organic phases are dried with sodium sulfate, the solvent is drawn off, and the residue is purified by chromatography with the mobile solvent system of methylene chloride/methanol: Yield 183 mg=96% of theory.

Example 9b

Tc-99m-Tricarbonyl Complex of N,N-bis-(2-methylthioethyl)-glycine-N'-propylamide 2 mg of N,N-bis-(2-methylthioethyl)-glycine-N'-propylamide (Example 9a) is dissolved in 1 ml of 0.1M disodium phosphate buffer (pH=8.5) and mixed with 37 MBq of $[^{99m}Tc(OH)_3(CO)_3]^{30}$ solution, produced in a way similar to R. Alberto et al., Achievements and Prospects of New Radiotracers, 1997, C3, p. 57 (Abstracts). It is incubated for 30 minutes at room temperature and then analyzed by means of HPLC: radiochemical purity >90%.

Example 9c

Stability Study of the Tc-99m-tricarbonyl Complex of N,N-bis-(2-methylthioethyl)-glycine-N'-propylamide The solution that is produced according to Example 9b is mixed with 20 mg of histidine and stirred for 1 hour at 50° C. Then, the radiochemical composition is studied with HPLC on an RP18 column: the chromatogram is unchanged. The tricarbonyl complex with histidine that is produced for comparison purposes has considerably shorter retention times.

What is claimed is:

1. A compound of general formula (1)

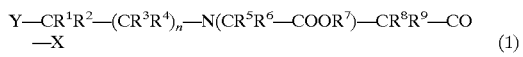

in which n stands for numbers 0, 1 or 2;

$R^1$, $R^2$, $R^3$, $R^4$, $R^5$, $R^6$, $R^8$ and $R^9$ are the same or different and in each case represent a hydrogen atom or an unbranched, a branched, a cyclic or a polycyclic $C_1$–$C_{60}$ alkyl, $C_1$–$C_{60}$ alkenyl, $C_5$–$C_{60}$ polyalkenyl, $C_1$–$C_{60}$ alkynyl; $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se;

$R^7$ stands for a hydrogen atom or an alkali cation or an alkaline-earth cation or a primary, secondary or tertiary ammonium;

X represents a radical O—$R^7$ or means a radical $NR^{10}R^{11}$, in which $R^{10}$ and $R^{11}$ are the same or different and in each case represent a hydrogen atom or an unbranched, a branched, a cyclic or a polycyclic $C_1$–$C_{60}$ alkyl, $C_1$–$C_{60}$ alkenyl, $C_1$–$C_{60}$ polyalkenyl, $C_1$–$C_{60}$ alkynyl, $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se; or $R^{10}$ and/or $R^{11}$ are the same or different and in each case represent a hydrogen atom, a peptide radical, a protein radical, a modified or an unmodified DNA or a RNA oligonucleotide radical, a modified or an unmodified aptamer radical or a PNA radical;

Y stands for an $R^{12}$—S radical, in which $R^{12}$ represents a hydrogen atom or an unbranched, a branched, a cyclic or a polycyclic $C_1$–$C_{60}$ alkyl, $C_1$–$C_{60}$ alkenyl, $C_5$–$C_{60}$ polyalkenyl, $C_1$–$C_{60}$ alkynyl, $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se; or $R^{12}$ represents a peptide radical, a protein radical, a modified or an unmodified DNA or a RNA-oligonucleotide radical, a modified or an unmodified aptamer radical or a PNA radical;

or Y stands for an $R^{13}R^{14}P$ radical, in which $R^{13}$ and $R^{14}$ are the same or different and in each case represent a hydrogen atom or an unbranched, a branched, a cyclic or a polycyclic $C_1$–$C_{60}$ alkyl, $C_1$–$C_{60}$ alkenyl, $C_5$–$C_{60}$ polyalkenyl, $C_1$–$C_{60}$ alkynyl, $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se;

and its complex with a tricarbonyl-technetium-I radical or a tricarbonyl-rhenium-I radical.

2. A compound according to claim 1, whereby radicals $R^1$, $R^2$, $R^3$, $R^4$, $R^5$, $R^6$, $R^8$ and $R^9$ in each case represent a hydrogen atom.

3. A compound according to claim 1, whereby $R^7$ stands for a hydrogen atom or an alkali cation or an alkaline earth cation.

4. A compound according to claim 1, whereby radical Y stands for a radical $R^{12}$—S, in which $R^{12}$ stands for an unbranched, a branched, a cyclic or a polycyclic, saturated or unsaturated $C_1$–$C_{60}$ alkyl radical.

5. A compound according to claim 4, whereby radical $R^{12}$ represents a $C_1$–$C_{10}$ alkyl chain.

6. A compound according to claim 1, whereby radical X stands for a group O—$R^7$, in which $R^7$ stands for a hydrogen atom or an alkali cation or an alkaline-earth cation or a primary, secondary or tertiary ammonium ion.

7. A compound according to claim 1, whereby radical X stands for a group $NR^{10}R^{11}$, in which $R^{10}$ and $R^{11}$ are the same or different and in each case represent a hydrogen atom, a peptide radical, a protein radical, a modified or an unmodified DNA or a RNA oligonucleotide radical, a modified or an unmodified aptamer radical or a PNA radical.

8. A compound according to claim 1, whereby radical X stands for a group $NR^{10}R^{11}$, in which $R^{10}$ and $R^{11}$ are the same or different and in each case stand for a hydrogen atom, an unbranched, a branched, a cyclic or a polycyclic, saturated or unsaturated $C_1$–$C_{60}$ alkyl radical.

9. A process for the production of a compound of general formula (I) according to claim 1, characterized in that a compound of general formula (II) is reacted with a compounds of general formula (III) according to the reaction diagram below

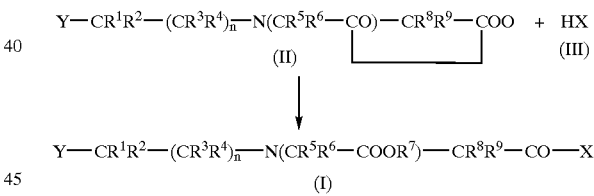

in which $R^1$, $R^2$, $R^3$, $R^4$, $R^5$, $R^6$, $R^7$, $R^8$ and $R^9$, are the same or different and in each case represent a hydrogen atom or an unbranched, a branched, a cyclic or a polycyclic $C_1$–$C_{60}$ alkyl, $C_1$–$C_{60}$ alkenyl, $C_5$–$C_{60}$ polyalkenyl, $C_1$–$C_{60}$ alkynyl; $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms O, N, S, P, As, or Se; or $R^7$ stands for a hydrogen atom or an alkali cation or an alkaline-earth cation or a primary, secondary or tertiary ammonium ion; and H in HX stands for a proton.

10. A radiopharmaceutical composition for non-invasive in-vivo visualization of a receptors and receptor-comprising tissue comprising a compound according to claim 1 and a pharmaceutically acceptable carrier.

11. A pharmaceutical agent, comprising a compound of general formula (I) according to claim 1 in solution or in freeze-dried form.

12. A compound of general formula (IV)

$$Y-CR^1R^2-(CR^3R^4)_n-N[(CR^5R^6)_2-Z]-CR^8R^9-CO-X \quad (IV)$$

in which n stands for numbers 0, 1 or 2;

$R^1, R^2, R^3, R^4, R^5, R^6, R^8$ and $R^9$ are the same or different and in each case represent a hydrogen atom or an unbranched, a branched, a cyclic or a polycyclic $C_1-C_{60}$ alkyl, $C_1-C_{60}$ alkenyl, $C_5-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selecTed from O, N, S, P, As, or Se;

X represents a radical $O-R^7$ or means a radical $NR^{10}R^{11}$, in which $R^{10}$ and $R^{11}$ are the same or different and in each case represent a hydrogen atom or an unbranched, a branched, a cyclic or a polycyclic $C_1-C_{60}$ alkyl, $C_1-C_{60}$ alkenyl, $C_1-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an interrupted and/or substituted by one or more heteroatoms selected from O, N, S, P, As, or Se; or $R^{10}$ and/or $R^{11}$ are the same or different and in each case represent a hydrogen atom, a peptide radical, a protein radical, a modified or an unmodified DNA or a RNA-oligonucleotide radical, a modified or an unmodified aptamer radical or a PNA radical;

Y stands for an $R^{12}-S$ radical, in which $R^{12}$ represents a hydrogen atom or an unbranched, a branched, a cyclic or a polycyclic $C_1-C_{60}$ alkyl, $C_1-C_{60}$ alkenyl, $C_5-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se; or $R^{12}$ represents a peptide radical, a protein radical, a modified or an unmodified DNA or a RNA oligonucleotide radical, a modified or an unmodified aptamer radical or a PNA radical;

or Y stands for an $R^{13}R^{14}P$ radical, in which $R^{13}$ and $R^{14}$ are the same or different and in each case represent a hydrogen atom or an unbranched, a branched, a cyclic or a polycyclic $C_1-C_{60}$ alkyl, $C_1-C_{60}$ alkenyl, $C_5-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se;

or Y stands for a monocyclic or a polycyclic heteroaromatic compound that contains at least one heteroatom selected from O, S, N and/or P;

Z stands for an $R^{12}-S$ radical, in which $R^{12}$ represents a hydrogen atom or an unbranched, a branched, a cyclic or a polycyclic $C_1-C_{60}$ alkyl, $C_1-C_{60}$ alkenyl, $C_5-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is $C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se;

or Z stands for an $R^{13}R^{14}P$ radical, in which $R^{13}$ and $R^{14}$ are the same or different and in each case represent a hydrogen atom or an unbranched, a branched, a cyclic or a polycyclic $C_1-C_{60}$ alkyl, $C_1-C_{60}$ alkenyl, $C_5-C_{60}$ polyalkenyl, $C_1-C_{60}$ alkynyl, $C_5-C_{60}$ polyalkynyl, $C_5-C_{60}$ aryl, $C_5-C_{60}$ alkylaryl or $C_5-C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms selected from O, N, S, P, As, or Se;

or Z stands for a monocyclic or a polycyclic heteroaromatic compound, which contains at least one heteroatom selected from O, S, N and/or P;

as well as its complex with a tricarbonyl-technetium-I or tricarbonyl-rhenium-I radical.

13. A compound according to claim 12, whereby radicals $R^1, R^2, R^3, R^4, R^5, R^6, R^8$ and $R^9$ in each case represent a hydrogen atom.

14. A compound according to claim 12, whereby radical Y stands for a radical $R^{12}-S$, in which $R^{13}$ stands for an unbranched, a branched, a cyclic or a polycyclic, a saturated or an unsaturated $C_1-C_{60}$ alkyl radical.

15. A compound according to claim 14, whereby radical $R^{12}$ represents a $C_1-C_{10}$ alkyl chain.

16. A compound according to claim 12, whereby radical X stands for a group $O-R^7$, in which $R^7$ stands for a hydrogen atom or an alkali cation or an alkaline-earth cation or a primary, secondary or tertiary ammonium ion.

17. A compound according to claim 12, whereby radical X stands for a group, $NR^{10}R^{11}$, in which $R^{10}$ and $R^{11}$ are the same or different and in each case represent a hydrogen atom, a peptide radical, a protein radical a modified or an unmodified DNA or a RNA oligonucleotide radical, a modified or an unmodified Aptamer radical or a PNA radical.

18. A compound according to claim 12, whereby radical X stands for a group $NR^{10}R^{11}$, in which $R^{10}$ and $R^{11}$ are the same or different and in each case stand for a hydrogen atom, an unbranched, a branched, a cyclic or a polycyclic, a saturated or an unsaturated $C_1-C_{60}$ alkyl radical.

19. A compound according to claim 12, wherein radical Z stands for a radical $R^{12}-S$, in which $R^{12}$ stands for an unbranched, a branched, a cyclic or a polycyclic, a saturated or an unsaturated $C_1-C_{60}$ alkyl radical.

20. A compound according to claim 19, whereby radical $R^{12}$ represents a $C_1-C_{10}$ alkyl chain.

21. A process for the production of a compound of general formula (IV) according to claim 1, wherein a compound of general formula (V) is reacted with a compound of general formula (III) according to the reaction diagram below:

$$Y-CR^1R^2-(CR^3R^4)_n-N[(CR^5R^6)_2-Z]-CR^8R^9-CO-X'(V)+$$
$$HX \quad (III)$$

$$Y-CR^1R^2-(CR^3R^4)_n-N[(CR^5R^6)_2-Z]-CR^8R^9-CO-X \quad (IV)$$

$R^1$, $R^2$, $R^3$, $R^4$, $R^5$, $R^6$, $R^7$, $R^8$ and $R^9$, are the same or different and in each case represent a hydrogen atom or an unbranched, a branched, a cyclic or a polycyclic $C_1$–$C_{60}$ alkyl, $C_1$–$C_{60}$ alkenyl, $C_5$–$C_{60}$ polyalkenyl, $C_1$–$C_{60}$ alkynyl; $C_5$–$C_{60}$ polyalkynyl, $C_5$–$C_{60}$ aryl, $C_5$–$C_{60}$ alkylaryl or $C_5$–$C_{60}$ arylalkyl radical, which optionally is substituted with a hydroxy, an oxo, a carboxy, an aminocarbonyl, an alkoxycarbonyl, an amino, an aldehyde or an alkoxy group with up to 20 carbon atoms and/or optionally is interrupted and/or substituted by one or more heteroatoms O, N, S, P, As, or Se; or $R^7$ stands for a hydrogen atom or an alkali cation or an alkaline-earth cation or a primary, secondary or tertiary ammonium ion; X' stands for a leaving group, and H in HX stands for a proton.

22. A method of producing a radiopharmaceutical composition for non-invasive in-vivo visualization of a receptor and a receptor-containing tissue comprising administrating to a patient a compound according to claim 12.

23. Pharmaceutical agent, wherein it contains a compound of general formula (IV) according to claim 12 in solution or in freeze-dried form.

24. A radiopharmaceutical composition according to claim 10 wherein the pharmaceutically acceptable carrier is an aqueous medium.

25. A radiopharmaceutical composition according to claim 24 wherein the aqueous medium comprises an additive.

26. A radiopharmaceutical composition according to claim 25 wherein the additive is a buffer, an electrolyte addition, or a stabilizer.

27. A radiopharmaceutical composition according to claim 26 wherein the electrolyte addition comprises sodium chloride.

28. A compound according to claim 1 wherein:

Y is an $R^{12}$—S radical, wherein $R^{12}$ is an unbranched $C_1$–$C_{10}$-alkyl radical;

each of $R^1$, $R^2$, $R^3$, $R^4$, $R^5$, $R^6$, $R^7$, $R^8$ and $R^9$ is a hydrogen atom, n=1, and X is a radical $NR^{10}R^{11}$, wherein $R^{10}$ is a hydrogen atom and $R^{11}$ is an unbranched $C_{1-60}$-alkyl radical.

29. A compound according to claim 28 wherein $R^{12}$ is an unbranched $C_2$-alkyl radical.

30. A compound according to claim 29 wherein $R^{11}$ is an unbranched $C_3$-alkyl radical.

31. A method of imaging a receptor or tissue comprising said receptor, comprising administering to a patient a compound of claim 1.

* * * * *

UNITED STATES PATENT AND TRADEMARK OFFICE
CERTIFICATE OF CORRECTION

PATENT NO.     : 6,488,909 B1
DATED          : December 3, 2002
INVENTOR(S)    : Christophe Hilger et al.

It is certified that error appears in the above-identified patent and that said Letters Patent is hereby corrected as shown below:

<u>Title page,</u>
Item [75], Inventors, reads "Stephan Hilger" should read -- Christoph Hilger --

<u>Column 15,</u>
Line 25, reads "ammonium;" should read -- ammonium ion --

<u>Column 16,</u>
Line 4, reads "and its complex" should read -- and their complex --
Line 35, reads "reacted with a compounds" should read -- reacted with a compound --
Line 65, reads "of a receptors" should read -- of a receptor --

<u>Column 17,</u>
Line 30, reads "an amino, an interrupted" should read -- an amino, an aldehyde or an alkoxy group with up to 20 atoms and/or optionally is interrupted --

<u>Column 18,</u>
Line 6, reads "optionally is C60 aryl, C5-C60 alkylaryl or C5-C60 arylalkyl radical, which optionally is substituted" should read -- optionally is substituted --
Line 18, reads "C1-C60 alkenyl" should read -- C1-C60 alkynyl --
Line 35, reads "in which R13" should read -- in which R12 --
Line 47, reads "a protein radical a modified" should read -- a protein radical, a modified --

Signed and Sealed this

Fourth Day of November, 2003

JAMES E. ROGAN
*Director of the United States Patent and Trademark Office*